United States Patent
Yang

(10) Patent No.: US 8,575,116 B1
(45) Date of Patent: Nov. 5, 2013

(54) POLYACETYLENIC COMPOUNDS FOR PROTECTING AGAINST PANCREATIC ISLET ATROPHY

(71) Applicant: Academia Sinica, Taipei (TW)

(72) Inventor: Wen-Chin Yang, Taichung County (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/964,583

(22) Filed: Aug. 12, 2013

Related U.S. Application Data

(62) Division of application No. 13/096,106, filed on Apr. 28, 2011, now Pat. No. 8,536,141.

(60) Provisional application No. 61/330,398, filed on May 3, 2010.

(51) Int. Cl.
*A61K 31/7028* (2006.01)

(52) U.S. Cl.
USPC .......................................................... 514/25

(58) Field of Classification Search
USPC .......................................................... 514/25
See application file for complete search history.

(56) References Cited

U.S. PATENT DOCUMENTS

| 7,763,285 B2 | 7/2010 | Yang et al. |
| 8,147,880 B2 | 4/2012 | Yang |
| 2008/0193568 A1 | 8/2008 | Yang et al. |
| 2011/0269702 A1 | 11/2011 | Yang |

*Primary Examiner* — Wu-Cheng Winston Shen
*Assistant Examiner* — Yih-Horng Shiao
(74) *Attorney, Agent, or Firm* — Hsiu-Ming Saunders; Intellectual Property Connections, Inc.

(57) ABSTRACT

Pharmaceutical compositions and methods for protecting against atrophy of pancreatic islets in a human with metabolic syndromes are disclosed. The method comprises administering to the mammal a pharmaceutical composition comprising a compound having a chemical structure of formula (I) in an effective amount and a pharmaceutically acceptable carrier:

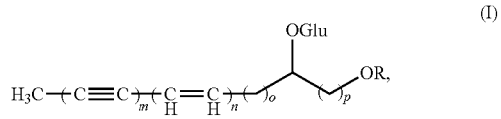

wherein
R is H or COCH2COOH;
m=3 or 4;
n=0 or 1;
o=2; and
p=1 or 2.

11 Claims, 14 Drawing Sheets

FIG. 1D-i
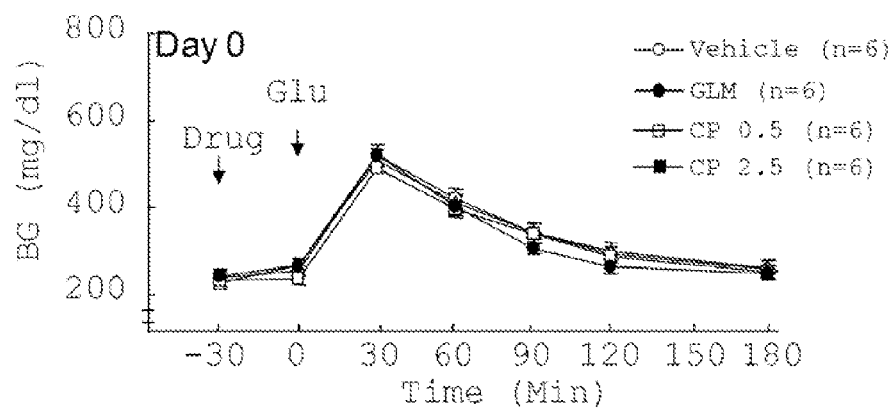
FIG. 1D-ii
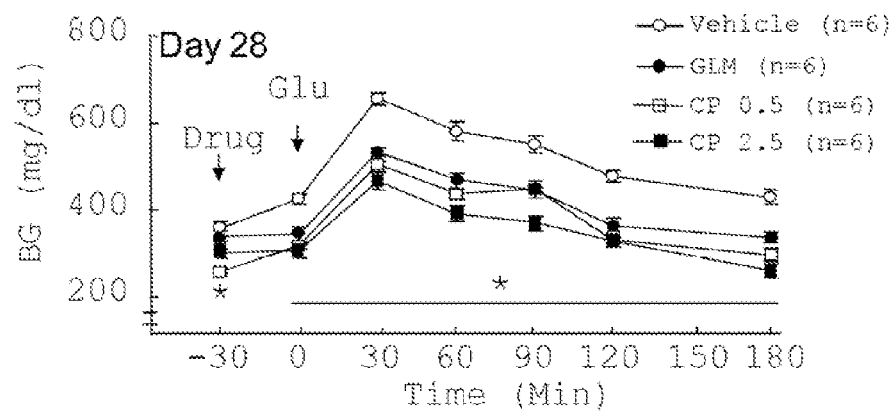
FIG. 1D-iii
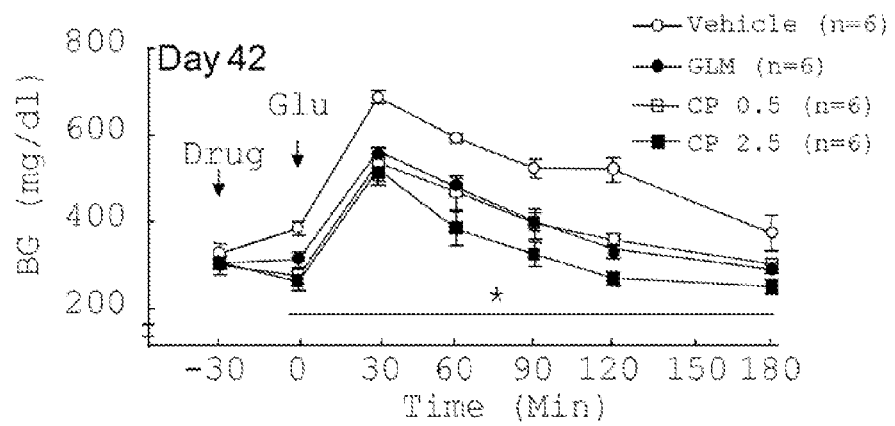

FIG. 3A-i
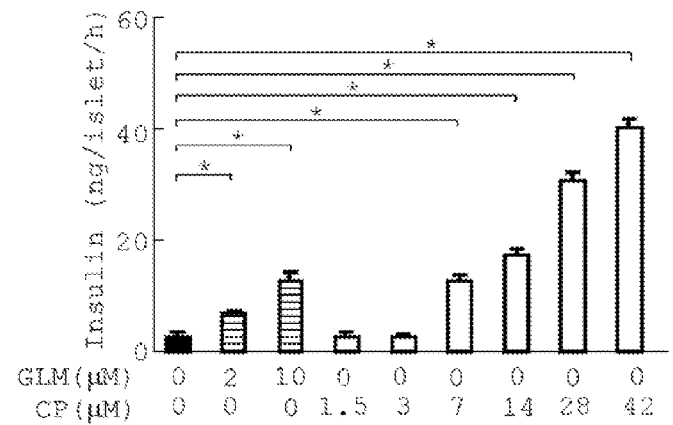
FIG. 3A-ii
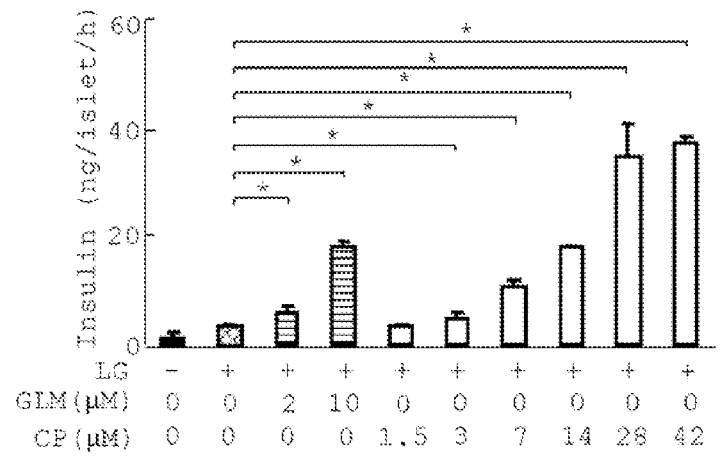
FIG. 3A-iii
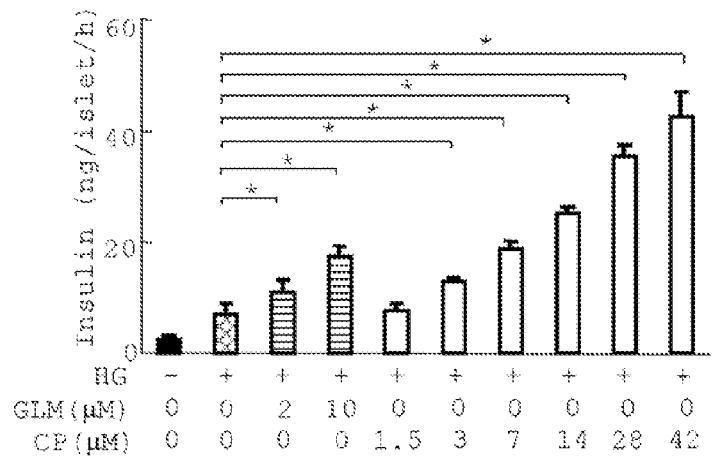

FIG. 6
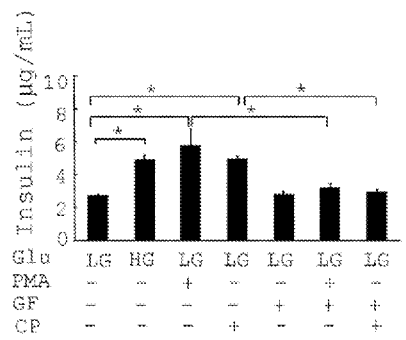
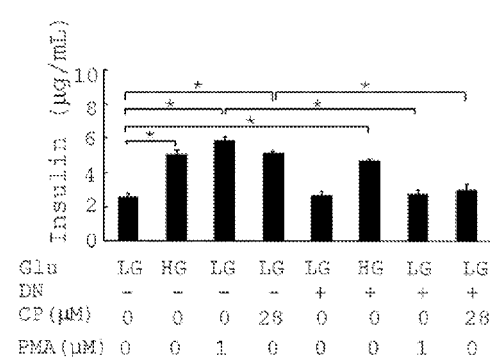
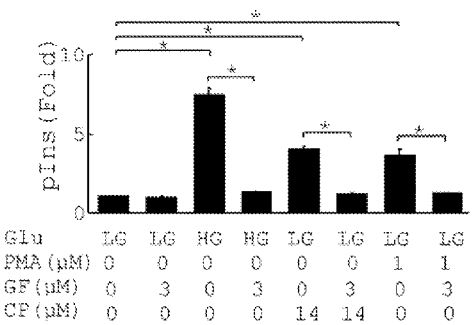
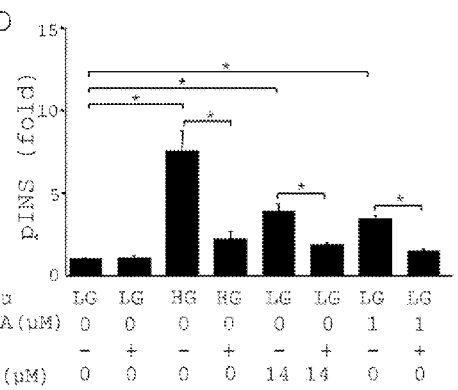

FIG. 7A-i
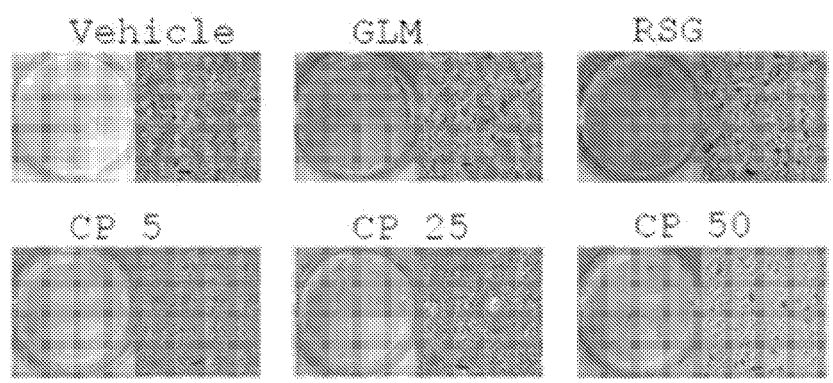
FIG. 7A-ii
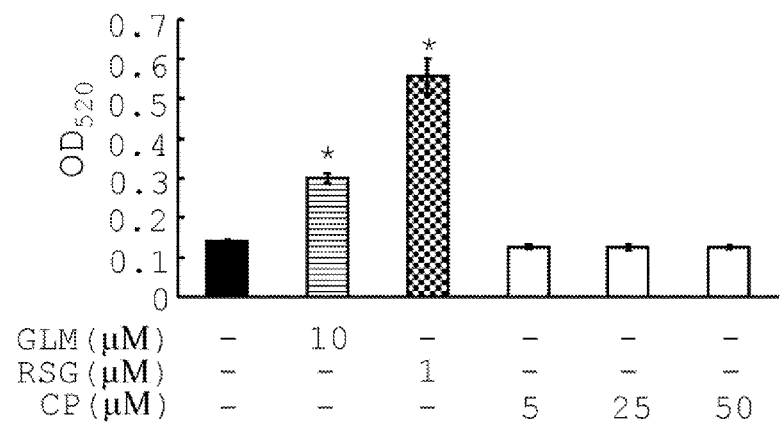

FIG. 7B-i
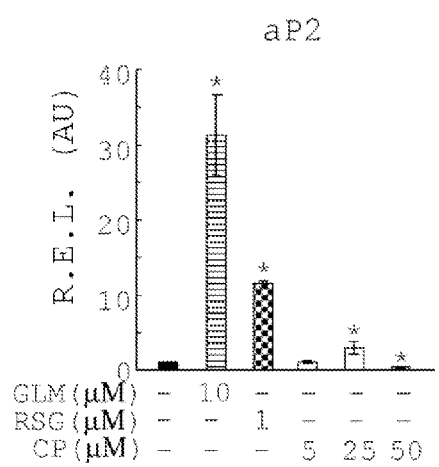
aP2
FIG. 7B-ii
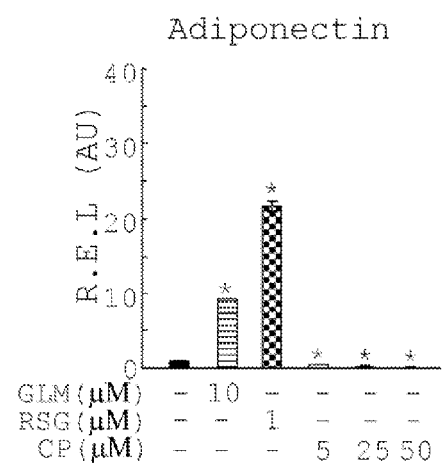
Adiponectin

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: insulin primer sense

<400> SEQUENCE: 1
tgcgggtcct ccacttcac                                              19

<210> SEQ ID NO 2
```

```
<211> LENGTH: 18
<212> TYPE: DNA
<213> ORGANISM: Artificial Sequence
<220> FEATURE:
<223> OTHER INFORMATION: insulin primer antisense

<400> SEQUENCE: 2
gccctgctcg tcctctgg                                                    18

<210> SEQ ID NO 3
<211> LENGTH: 20
<212> TYPE: DNA
<213> ORGANISM: Artificial Sequence
<220> FEATURE:
<223> OTHER INFORMATION: L13 primer sense

<400> SEQUENCE: 3
agataccaca ccaaggtccg                                                  20

<210> SEQ ID NO 4
<211> LENGTH: 18
<212> TYPE: DNA
<213> ORGANISM: Artificial Sequence
<220> FEATURE:
<223> OTHER INFORMATION: L13 primer antisense

<400> SEQUENCE: 4
ggagcagaag gcttcctg                                                    18

<210> SEQ ID NO 5
<211> LENGTH: 22
<212> TYPE: DNA
<213> ORGANISM: Artificial Sequence
<220> FEATURE:
<223> OTHER INFORMATION: aP2 primer sense

<400> SEQUENCE: 5
caaaatgtgt gatgcctttg tg                                               22

<210> SEQ ID NO 6
<211> LENGTH: 20
<212> TYPE: DNA
<213> ORGANISM: Artificial Sequence
<220> FEATURE:
<223> OTHER INFORMATION: aP2 primer antisense

<400> SEQUENCE: 6
ctcttccttt ggctcatgcc                                                  20

<210> SEQ ID NO 7
<211> LENGTH: 20
<212> TYPE: DNA
<213> ORGANISM: Artificial Sequence
<220> FEATURE:
<223> OTHER INFORMATION: adiponectin primer sense

<400> SEQUENCE: 7
gatggcagag atggcactcc                                                  20

<210> SEQ ID NO 8
<211> LENGTH: 20
<212> TYPE: DNA
<213> ORGANISM: Artificial Sequence
<220> FEATURE:
<223> OTHER INFORMATION: adiponectin primer antisense

<400> SEQUENCE: 8
```

```
cttgccagtg ctgccgtcat                                              20

<210> SEQ ID NO 9
<211> LENGTH: 20
<212> TYPE: DNA
<213> ORGANISM: Artificial Sequence
<220> FEATURE:
<223> OTHER INFORMATION: GAPDH primer sense

<400> SEQUENCE: 9
accacagtcc atgccatcac                                              20

<210> SEQ ID NO 10
<211> LENGTH: 20
<212> TYPE: DNA
<213> ORGANISM: Artificial Sequence
<220> FEATURE:
<223> OTHER INFORMATION: GAPDH primer antisense

<400> SEQUENCE: 10
tccaccaccc tgttgctgta                                              20
```

POLYACETYLENIC COMPOUNDS FOR PROTECTING AGAINST PANCREATIC ISLET ATROPHY

REFERENCE TO RELATED APPLICATION

The present application is a divisional of and claims priority to U.S. application Ser. No. 13/096,106, filed Apr. 28, 2011, which status is allowed and claims priority to U.S. Provisional Application Ser. No. 61/330,398, filed May 3, 2010, all of which are herein incorporated by reference in their entireties.

FIELD OF THE INVENTION

The present invention relates generally to polyacetylenic compounds, and more specifically to polyacetylenic compounds for protecting against islet atrophy.

BACKGROUND OF THE INVENTION

Diabetes is a life-threatening metabolic disease, afflicting around 3% of the world population. Over 90% of the diabetic populations are diagnosed with type-2 diabetes (T2D) mellitus. The current anti-hyperglycemic drugs are insulin secretagogues, insulin sensitizers, inhibitors of sugar cleavage, and glucagon-like peptide-1 (GLP-1), each of which controls homeostasis of blood sugar by a different mechanism. Common drawbacks of these drugs include side effects, decreased efficacy over time, low cost-effectiveness and only partial anti-diabetic effect of each individual drug. Secretagogues that have the ability to prevent adverse effects (e.g., weight gain, hypoglycemia) or stimulate insulin biosynthesis or protect β-cells from death are rare (Krentz et al., 2005; Purnell et al., 2003). Glucagon-like peptide-1 (GLP-1), an injectable peptide drug, may be the only one reported to fit these criteria (Egan et al., 2003). In view of patients' welfare, there is still a need for development of anti-diabetics for decrease in hypoglycemia, enhancement of insulin synthesis and β-cell protection.

Plants are an extraordinary resource for anti-diabetic remedies. One prestigious example may be metformin, a derivative of the phytochemical, guanidine, from French lilac and known as the insulin sensitizer for T2D. A plant from the Asteraceae family, *Bidens pilosa*, which was anti-diabetic in alloxan-treated mice, has been used to treat patients with diabetes in America, Africa, and Asia. Two polyacetylenes from *B. pilosa* have since been demonstrated to be anti-diabetic by different laboratories (Chang et al., 2004, Ubillas et al., 2000). Cytopiloyne was recently identified as the most potent polyacetylene in *B. pilosa* in prevention of type 1 diabetes via T-cell regulation (Chang et al., 2007). *B. pilosa* and its three polyacetylenes showed glucose-lowering activities in diabetic mice (Chien et al., 2009; Hsu et al., 2009; Ubillas et al., 2000). However, the anti-diabetic mechanism of these three polyacetylenes is not known.

SUMMARY OF THE INVENTION

In one aspect, the invention relates to a method of protecting against atrophy of pancreatic islets in a mammal in need thereof, which comprises administering to the mammal a pharmaceutical composition comprising a compound having a chemical structure of formula (I) in an effective amount and a pharmaceutically acceptable carrier:

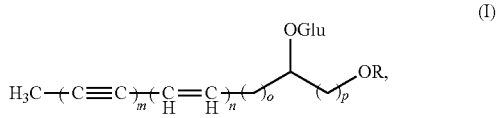

wherein
R is H or COCH2COOH;
m=3 or 4;
n=0 or 1;
o=2; and
p=1 or 2.

In another aspect, the invention relates to a method of protecting against atrophy of pancreatic β-cells in a mammal in need thereof, which comprises administering to the mammal a composition comprising cytopiloyne and a pharmaceutically acceptable carrier.

Further in another aspect, the invention relates to a method of protecting against atrophy of pancreatic islets in a mammal in need thereof, which comprises administering to the mammal a pharmaceutical composition comprising a polyacetylenic compound, wherein the polyacetylenic compound is at least one chosen from:

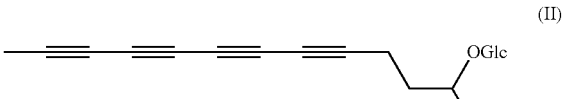

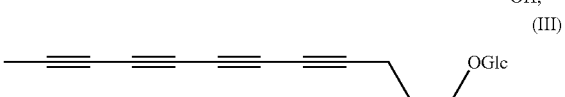

and

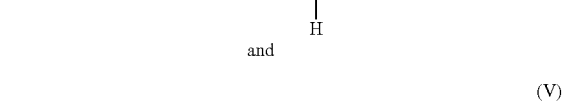

R = COCH2COOH

Yet in another aspect, the invention relates to a pharmaceutical kit comprising:
(a) a composition comprising a compound having a chemical structure of formula (I) in an effective amount and a pharmaceutically acceptable carrier:

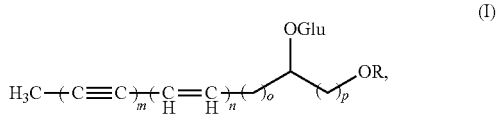

wherein

R is H or COCH2COOH;

m=3 or 4;

n=0 or 1;

o=2; and p=1 or 2; and (b) an insert containing instructions on the method of preventing protecting against atrophy of pancreatic islets in a mammal in need thereof.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 1A-F show the anti-diabetic effects of cytopiloyne in db/db mice during long-term treatment. (A) Chemical structure of cytopiloyne (2-β-$_D$-glucopyranosyloxy-1-hydroxytrideca-5,7,9,11-tetrayne). (B) Four groups of 6-to-8-week-old diabetic db/db mice were tube-fed with vehicle, cytopiloyne (CP, 0.5 and 2.5 mgkg$^{-1}$ day$^{-1}$) or glimepiride (GLM, 2.5 mgkg$^{-1}$ day$^{-1}$) from 0 to 42 days post-treatment. Blood glucose (BG) levels in these mice were measured. (C) Blood insulin levels from the mice of FIG. 1B. (D) IPGTT was performed in the db/db mice of FIG. 1B on day 0, 28 and 42, and blood glucose levels were monitored for 3.5 h. (E) The percentage of glycosylated HbA$_{1c}$ of whole blood from the mice of FIG. 1B on day 0 and 42. (F) Pancreata of 8- and 16-week-old db/db males, which had received the same treatment as FIG. 1B for 2 (images a-h) and 10 (images i-p) weeks, were stained with hematoxylin and eosin (H&E, images a, c, e, g, i, k, m and o) or hematoxylin and anti-insulin (H&I, images b, d, f, h, j, l, n and p). The arrowheads indicate pancreatic islets. Scale bars, 200 µm. Results from 3 independent experiments are expressed as mean±SEM, and P<0.05 was considered to be statistically significant (*). The number of mice (n) is indicated in parentheses.

FIGS. 3A-C show cytopiloyne-mediated insulin release depends on pancreatic islet cells. (A) Rat pancreatic islet cells were incubated with glucose-free KRB buffer containing vehicle or cytopiloyne at 1.5, 3, 7, 14, 28 and 42 µM (FIG. 3A-i). Similarly, rat pancreatic islet cells were incubated with KRB buffer containing vehicle, glimepiride (GLM, 10 µM) or cytopiloyne at 1.5, 3, 7, 14, 28 and 42 µM in the presence of 3.3 mM glucose (LG, FIG. 3A-ii) or 16.7 mM glucose (HG, FIG. 3A-iii). The insulin levels were determined using an insulin ELISA kit. The data presented as mean±SEM of 3 independent experiments. (B) Fed C57BL mice, which had already received an injection of STZ, were administered with an oral dose of vehicle, cytopiloyne (CP, 0.1, 0.5 and 2.5 mgkg$^{-1}$), and an intraperitoneal injection of insulin (Ins, 2.5 IUkg$^{-1}$). Blood sugar levels in the STZ-treated mice were determined using a glucometer. (C) C57BL mice, which had already received STZ, were orally administered with a single dose of vehicle, cytopiloyne (CP, 0.5 and 2.5 mgkg$^{-1}$), glimepiride (GLM, 2.5 mgkg$^{-1}$), or metformin (60 mgkg$^{-1}$), followed by an intraperitoneal injection with insulin (Ins). Blood sugar levels in the STZ-treated mice were determined using a glucometer. All the results from 3 independent experiments are expressed as mean±SEM, and P<0.05 was considered to be statistically significant (*). The number of mice (n) is indicated in parentheses.

FIGS. 6A-D shows cytopiloyne-mediated insulin secretion and expression is abolished by dominant-negative mund inhibitor of PKCα. (A) RIN-M5F cells were grown in medium with 16.7 mM (HG) or 3.3 mM glucose (LG) in the presence of PMA. GF and cytopiloyne. The insulin level of the supernatants was determined using an ELISA kit. (B) RIN-M5F cells were transfected with 5 µg of dominant-negative PKCα or control plasmid grown in medium with 16.7 mM (HG) or 3.3 mM glucose (LG) in the presence of PMA (1 µM), GF109203X (3 µM) or cytopiloyne. The insulin level of the supernatants was determined using an ELISA kit. (C) HIT-T15 cells were transfected with phINS-Luc and pRL-TK plasmids. The cells were grown in medium with 16.7 mM (HG) or 3.3 mM glucose (LG) in the absence or presence of PMA, GF109203X and cytopiloyne. The cell lysates were subjected to dual luciferase assays. (D) HIT-T15 cells were transfected with vehicle or dominant-negative PKCα plasmid together with phINS-Luc and pRL-TK plasmids. The cells were grown in medium with 16.7 mM (HG) or 3.3 mM glucose (LG) in the absence or presence of PMA and cytopiloyne. The cell lysates were subjected to dual luciferase assays.

FIGS. 7A-B show the effects of cytopiloyne on adipogenesis in differentiating 3T3-L1 cells. (A) 3T3-L1 cells were incubated with vehicle, glimepiride (GLM, 10 μM), rosiglitazone (RSG, 1 μM) or cytopiloyne (CP, 5, 25 and 50 μM), for 10 days. Lipid droplets from the above cells (A) were visualized by Oil red O staining and examined by light microscopy (top panel). Scale bars, 10 μm. Oil red O extracted from these cells was quantified by optical density at 520 nm (bottom panel). (B) The relative expression level (R.E.L.) of aP2 or adiponectin mRNA relative to that of GAPDH mRNA in the cells (A) was determined using real-time RT-PCR.

DETAILED DESCRIPTION OF THE INVENTION

Definitions

Figure 1A:
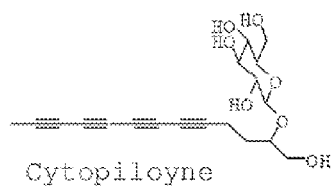

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "to prevent" or "preventing" shall generally refer to different degrees of stoppage of action or progress. To prevent is to lessen the degree or to stop something effectually, or both. The term "to prevent" means significantly improving the condition relative to a control. A control means a subject that is without a preventive treatment.

The terms "a glycosylated hemoglobin $A_{1C}$," "$HbA_{1c}$," "Hemoglobin $A_{1C}$," "$A_1$" and "$A_{1C}$" are interchangeable.

The term "Insulin resistance (IR)" shall generally mean a condition in which body cells become less sensitive to the glucose-lowering effects of the hormone insulin.

The term "preserving and/or maintaining" shall generally mean keeping alive or in existence, keeping safe from harm or injury, or protecting.

Pre-Diabetes

Pre-diabetes is a condition in which blood glucose levels are higher than normal but not high enough for a diagnosis of diabetes. This condition is sometimes called impaired fasting glucose (IFG) or impaired glucose tolerance (IGT), depending on the test used to diagnose it. The U.S. Department of Health and Human Services estimates that about one in four U.S. adults aged 20 years or older—or 57 million people—had pre-diabetes in 2007.

People with pre-diabetes are at increased risk of developing type 2 diabetes, formerly called adult-onset diabetes or noninsulin-dependent diabetes. Type 2 diabetes is sometimes defined as the form of diabetes that develops when the body does not respond properly to insulin, as opposed to type I diabetes, in which the pancreas makes little or no insulin.

Studies have shown that most people with pre-diabetes develop type 2 diabetes within 10 years, unless they lose 5 to 7 percent of their body weight—about 10 to 15 pounds for someone who weighs 200 pounds—by making changes in their diet and level of physical activity. People with pre-diabetes also are at increased risk of developing cardiovascular disease.

Diabetes and pre-diabetes can be detected with one of the following tests: a) Fasting glucose test. This test measures blood glucose in people who have not eaten anything for at least 8 hours. This test is most reliable when done in the morning. Fasting glucose levels of 100 to 125 mg/dL are above normal but not high enough to be called diabetes. This condition is called pre-diabetes or IFG. People with IFG often have had insulin resistance for some time. They are much more likely to develop diabetes than people with normal blood glucose levels. b) Glucose tolerance test. This test measures blood glucose after people fast for at least 8 hours and 2 hours after they drink a sweet liquid provided by a doctor or laboratory. A blood glucose level between 140 and 199 mg/dL means glucose tolerance is not normal but is not high enough for a diagnosis of diabetes. This form of pre-diabetes is called IGT and, like IFG, it points toward a history of insulin resistance and a risk for developing diabetes.

People whose test results indicate they have pre-diabetes should have their blood glucose levels checked again in 1 to 2 years.

Metabolic Syndrome

Fifty million Americans now carry the diagnosis of metabolic syndrome, a cluster of life-shortening morbidities that include type 2 diabetes (T2D). Metabolic syndrome is defined as the presence of any three of the following conditions: a) waist measurement of 40 inches or more for men and 35 inches or more for women; b) triglyceride levels of 150 milligrams per deciliter (mg/dL) or above, or taking medication for elevated triglyceride levels; c) HDL, or "good," cholesterol level below 40 mg/dL for men and below 50 mg/dL for women, or taking medication for low HDL levels: d) blood pressure levels of 130/85 or above, or taking medication for elevated blood pressure levels; e) fasting blood glucose levels of 100 mg/dL or above, or taking medication for elevated blood glucose levels.

Pre-diabetes and diabetes are now understood as a continuum, with cut-offs representing different stages of expression of disease or its complications. Early intervention in this continuum at low dose of anti-hyperglycemic agent would be effective. Metabolic syndrome is a pre-diabetes state which incorporates factors other than hyperglycemia. To reduce the risk for β-cell atrophy, there is a need for the intervention as discovered by the inventors.

In one aspect, the invention relates to a method of protecting against atrophy of pancreatic islets in a mammal in need thereof, which comprises administering to the mammal a pharmaceutical composition comprising a compound having a chemical structure of formula (I) in an effective amount and a pharmaceutically acceptable carrier:

$$H_3C-(C\equiv C)_m-(C=C)_n-()_o-()_p-OR \text{ with OGlu}$$ (I)

wherein
R is H or COCH2COOH;
m=3 or 4;
n=0 or 1;
o=2; and
p=1 or 2.

In one embodiment of the invention, the mammal has metabolic syndrome, or prediabetes, or diabetes.

In another embodiment of the invention, the composition comprises cytopiloyne having a chemical structure of formula (II):

(II) — structure with OGlc and OH

In another embodiment of the invention, the composition comprises a *Bidens pilosa* extract comprising cytopiloyne.

In another embodiment of the invention, the composition comprises cytopiloyne purified from a *Bidens pilosa* extract.

Further in another embodiment of the invention, the aforementioned method is free of the step of causing an increase in body weight and/or free of the step of causing accumulation of lipid contents in the adipose tissues of the mammal.

Further in another embodiment of the invention, the aforementioned method is free of the step of causing development of insulin resistance in the mammal.

In another aspect, the invention relates to a method of protecting against atrophy of pancreatic β-cells in a mammal in need thereof, which comprises administering to the mammal a composition comprising cytopiloyne and a pharmaceutically acceptable carrier.

Further in another aspect, the invention relates to a method of protecting against atrophy of pancreatic islets in a mammal in need thereof, which comprises administering to the mammal a pharmaceutical composition comprising a polyacetylenic compound, wherein the polyacetylenic compound is at least one chosen from:

(II) — structure with OGlc and OH (III) — structure with OGlc and OR (IV) — structure with OGlc and OR and (V) — structure with OGlc and OR

R = COCH2COOH

Yet in another aspect, the invention relates to a pharmaceutical kit comprising:

(a) a composition comprising a compound having a chemical structure of formula (I) in an effective amount and a pharmaceutically acceptable carrier:

$$H_3C-(C\equiv C)_m-(C=C)_n-()_o-()_p-OR \text{ with OGlu}$$ (I)

wherein
R is H or COCH2COOH;
m=3 or 4;
n=0 or 1;
o=2; and
p=1 or 2; and (c) an insert containing instructions on the method of preventing protecting against atrophy of pancreatic islets in a mammal in need thereof.

In one embodiment of the invention, the insert contains instructions on the method of preventing protecting against atrophy of pancreatic islets in a mammal with metabolic syndrome, prediabetes, or diabetes.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Cytopiloyne (chemical structure of formula II) has anti-diabetic activity shown by glycemic control, glucose tolerance and glycosylated hemoglobulin $A_{1c}$ ($HbA_{1c}$) levels, in db/db mice, a type 2 diabetes mouse model. Consistent with this, cytopiloyne promoted insulin biosynthesis/release and maintained pancreatic islet structure. In addition, cytopiloyne did not induce adipogenesis in adipocytes. Polyacetylenic compounds having chemical structure of formula III, IV or V have also been found present in *Bidens pilosa* and identified as active anti-hyperglycemic agents (see Japanese patent application No. 2002245569, publication date 20040318, which is herein incorporated by reference in its entirety).

Methods

Chemicals, Cells and Animals

DMSO, streptozocin (STZ), metformin, glimepiride, Oil red O, dexamethasone, isobutylmethylxanthine, rosiglitazone, brefeldin A, hematoxylin, eosin, phorbol 12-myristate 13-acetate (PMA), glimepiride, and diaminobenzidine tetrahydrochloride were purchased from Sigma-Aldrich (St Louis, Mo., USA). H-myristic acid was purchased from Perkin-Elmer (Waltham, Mass., USA). Insulin and anti-insulin antibody (H-86) were purchased from Novo Nordisk (Princeton, N.J., USA) and Santa Cruz Biotechnology (Santa Cruz, Calif., USA). Cytopiloyne was prepared from a water extract of *B. pilosa* by RP-18 silica HPLC (purity >95%) as previously published (See Chang et al. (2007); Chang et al. (2004); U.S. Patent Publication Nos: 20100310587; 20100204166; 20090062216; 20080193568; 20070053998; 20070048395; 20070048394, all of which are herein incorporated by reference in their entireties). Two rat β-cell lines, HIT-T15 β-cells (CRL-1777) and RIN-m5F (CRL-11605) cells, and a mouse pre-adipocyte line, 3T3-L1 (CL-173), were obtained from American Type Culture Collection. Primary pancreatic islet cells were isolated from fasted Wistar rats (NLAC, Taipei, Taiwan). The db/db mice (Jackson Laboratory, Bar Harbor, Me., USA) share many, if not all, pathological features with T2D patients. All the animals were maintained in the institutional animal facility and handled according to the guidelines of the Academia Sinica Institutional Animal Care and Utilization Committee.

Drug Administration in db/db Mice

For single-dose administration, diabetic db/db males aged 6 to 8 weeks, with free access to food, were grouped and tube-fed with 0.2 ml vehicle (1 µl DMSO per 1 ml of PBS), cytopiloyne (0.1, 0.5 and 2.5 mgkg$^{-1}$ body weight (BW)) or glimepiride (2.5 mgkg$^{-1}$ BW). After 0.5 h, the levels of postprandial blood sugar and insulin from the mice were monitored for additional 4 h. For continued administration, diabetic db/db males were grouped and tube-fed with vehicle, cytopiloyne (0.5 or 2.5 mgkg$^{-1}$ day$^{-1}$) or glimepiride (2.5 mg kg$^{-1}$ day$^{-1}$) for the indicated time, while levels of blood sugar, insulin, and glycosylated $HbA_{1c}$, and glucose tolerance in these mice were determined. To evaluate the prophylaxis of diabetes, diabetes-free db/db mice at 4 weeks of age were tube-fed with vehicle or cytopiloyne (CP, 0.5 mgkg$^{-1}$), once a day, for 4 weeks. Unless indicated otherwise, the mice were fasted for 16 h, then Postprandial blood glucose and insulin in these mice were measured.

Drug Administration in SIZ-Treated Mice

To deplete pancreatic β-cells in mice, 6-week-old C57BL females (NLAC, Taipei, Taiwan) were intraperitoneally injected with STZ at 200 mgkg$^{-1}$. STZ-treated females with postprandial blood sugar over 500 mgdl$^{-1}$ were grouped. Each group was either tube-fed with vehicle (1 µl DMSO per 1 ml of PBS), cytopiloyne (0.1, 0.5 and 2.5 mgkg$^{-1}$), or glimepiride (2.5 mgkg$^{-1}$), or injected with insulin at 2.5 IUkg$^{-1}$ BW. Blood glucose levels were monitored for 4 h. To distinguish sensitizer activity from releaser activity of cytopiloyne, STZ-treated C57BL mice were tube-fed with vehicle, glimepiride (2.5 mgkg$^{-1}$), metformin (60 mgkg$^{-1}$) or cytopiloyne (0.5 and 2.5 mgkg$^{-1}$) 1 h before insulin injection (2.5 IUkg$^{-1}$). Blood glucose levels in the mice were monitored from 0 to 4 h after insulin injection.

Measurement of Glucose, Insulin and $HbA_{1c}$

Glucose levels in mouse blood samples were measured using an Elite® glucometer (Bayer, Pittsburgh, Pa., USA). Insulin levels in blood samples or islet cell supernatants were determined by ELISA assays (Mercodia, Uppsala, Sweden). The levels of glycosylated $HbA_{1c}$ in mouse blood samples were measured using DCA 2000 analyzer (Bayer, Pittsburgh, Pa., USA).

Insulin Release

Pancreatic islets (10 isletsml$^{-1}$) from fasted male Wistar rats were incubated with KRB buffer containing vehicle (1 µl DMSO per ml KRB buffer), glimepiride or cytopiloyne in the absence or presence of glucose for 30 min. The KRB buffer was then collected for ELISA assays.

Intraperitoneal Glucose Tolerance Test (IPGTT)

Male db/db mice were administered either vehicle, cytopiloyne at 0.5 and 2.5 mgkg$^{-1}$ day$^{-1}$ or glimepiride at 2.5 mgkg$^{-1}$ day$^{-1}$ for the indicated time. The mice were fasted for 16 h before glucose tolerance test. On day 0, 28 and 42, each group received an oral dose (0.2 ml) of vehicle (1 µl DMSO per 1 ml of PBS), glimepiride or cytopiloyne (time 0) and, 0.5 h later, one intraperitoneal injection with glucose (0.5 gkg$^{-1}$). The levels of blood sugar were monitored from −0.5 to 3 h after glucose administration.

Immunohistochemistry

Pancreata from db/db males with continuous drug administration were snap frozen in OCT™ compound and stained with hematoxylin and eosin or anti-insulin antibody, followed by diaminobenzidine tetrahydrochloride development. Multiple parallel sections of each pancreas were analyzed by light microscopy.

Intracellular Staining for Insulin

Rat pancreatic islets were incubated with vehicle alone (1 µl DMSO per 1 ml of PBS), cytopiloyne, or glimepiride for 24 h. The islets were disrupted into individual cells and underwent intracellular staining with anti-insulin antibody and FACS analysis.

Real-Time RT-PCR Analysis

Rat pancreatic islets were incubated with vehicle (1 µl DMSO per 1 ml of PBS), cytopiloyne or glimepiride for 24 h. Total RNA isolated from these islets were extracted and converted to cDNA. Real-time RT-PCR was performed with the above cDNA with insulin primers, 5'-TGCGGGTCCTC-CACTTCAC-3' (SEQ ID NO: 1) and 5'-GCCCTGCTCGTC-CTCTGG-3' (SEQ ID NO: 2), or L13 primers, 5'-AGA TAC CAC ACC AAG GTC CG-3' (SEQ ID NO: 3) and 5'-GGA GCA GAA GGC TTC CTG-3' (SEQ ID NO: 4). For mouse 3T3-L1 cells, a similar procedure was adopted. Real-time RT-PCR was performed with the cDNA of differentiating 3T3-L1 cells with aP2 primers, 5'-CAAAATGTGTGATGC-CTTTGTG-3' (SEQ ID NO: 5) and 5'-CTCTTCCTTTG-GCTCATGCC-3' (SEQ ID NO: 6), adiponectin primers, 5'-GATGGCAGAGATGGCACTCC-3' (SEQ ID NO: 7) and 5'-CTTGCCAGTGCTGCCGTCAT-3' (SEQ ID NO: 8), and GAPDH primers, 5'-ACCACAGTCCATGCCATCAC-3' (SEQ ID NO: 9) and 5'-TCCACCACCCTGTTGCTGTA-3' (SEQ ID NO: 10).

Transfection and Luciferase Assays

Plasmids phINS-Luc and pRL-TK contain a human insulin promoter (2347 bp) from phINS-DCR3 vector linked to a firefly luciferase gene and the thymidine kinase promoter linked to *Renilla* luciferase reporter gene, respectively. Dominant-negative PKCα, phINS-Luc and/or pRL-TK were transfected into HIT-T15 cells with lipofectamine or electroporation. After a 24 h recovery, the cells were treated with vehicle (1 μl DMSO per 1 ml of medium), glucose, GF109203X (PKC inhibitor), glimepiride or cytopiloyne for additional 24 h, followed by dual luciferase assays.

Detection of Intracellular Calcium

RIN-m5F cells were pre-loaded with Fura 2-AM (5 μM) in modified Krebs-Henseleit buffer for 30 min at 25° C. After washing, the cells were stimulated with 16.7 mM glucose or cytopiloyne (7, 14 and 28 μM). Intracellular calcium of the cells was measured using a fluorescence spectrophotometer (CAF 110, Jasco, Tokyo, Japan) at excitation wavelengths of 340 and 380 nm and an emission wavelength of 500 nm. The ratio of fluorescence intensity at 340 nm to that at 380 nm represents the level of intracellular calcium.

Extraction and Measurement of DAG

RIN-m5F cells were incubated with $^3$H-myristic acid (5 CimL$^{-1}$) for 16 hours. After washing, the cells were treated with glucose, cytopiloyne, PMA and glimepiride. Total lipids were extracted as previously described. Radioactive DAG was separated on a silica thin layer plate with the first developer of ethylacetate: acetic acid: triethylpentane (9:2:5) and the second developer of hexane: diethylether: methanol: acetic acid (90:20:3:2). The spot of DAG was visualized with iodine vapor and identified by DAG standard.

Adipogenesis Assays

3T3-L1 cells were grown in adipogenesis progression medium (DMEM medium containing 10% fetal bovine serum, dexamethasone, isobutylmethylxanthine and insulin) for 2 days. The cells were incubated with the above medium and vehicle (1 μl DMSO per 1 ml of medium), glimepiride (10 μM), rosiglitazone (1 μM) or cytopiloyne (5, 25 and 50 μM) for an additional 8 days. One aliquot of the above cells underwent RT-PCR analysis. The other was microscopically checked for lipid accumulation, followed by Oil red O staining and measurement of the OD at 520 nm.

Statistical Analysis

Data from three independent experiments or more were presented as mean±SEM. ANOVA test was used for statistical analysis of differences between groups, and *P<0.05 was considered to be statistically significant.

Results

Beneficial Effect of Cytopiloyne in Glucose Lowering, Glucose Tolerance Test, Glycosylation of HbA$_{1c}$ and Islet Preservation One-dose effect of cytopiloyne on diabetic db/db mice was examined. Like glimepiride (2.5 mgkg$^{-1}$), cytopiloyne at the dose of 0.1, 0.5 and 2.5 mgkg$^{-1}$ significantly reduced postprandial blood glucose levels in diabetic db/db mice (Table 1). This reduction was dose-dependent. Blood insulin levels were also monitored in the mice. Both glimepiride and cytopiloyne significantly elevated the blood insulin levels in db/db mice compared to the vehicle alone (Table 2). These data proved that a single dose of cytopiloyne had anti-hyperglycemic and insulin-releasing effects on db/db mice.

The long-term therapeutic effects of cytopiloyne in diabetic db/db mice were also investigated. It was found that 0.5 mgkg$^{-1}$ cytopiloyne had similar blood sugar-lowering effects on fed db/db mice as glimepiride at 2.5 mgkg$^{-1}$ (FIG. 1B). Cytopiloyne at 2.5 mgkg$^{-1}$ was slightly therapeutically better than glimepiride at 2.5 mgkg$^{-1}$. Cytopiloyne increased blood insulin levels to a greater extent than glimepiride and this increase was dose-dependent (FIG. 1C). The effect of cytopiloyne on glucose tolerance was also evaluated. IPGTT assays showed no difference in glucose tolerance in treated and control mice on day 0 (FIG. 1D-*i*). In contrast, cytopiloyne treatment for 6 weeks improved glucose tolerance in db/db mice to a greater extent than glimepiride at the same dose (2.5 mgkg$^{-1}$) (Day 42, FIG. 1D-*iii*).

The glycosylated HbA$_{1c}$ has been known to be an excellent indicator of long-term glycemic control. The percentage of glycosylated HbA$_{1c}$ in db/db mice following different treatments were investigated. In the blood from 6- to 8-week-old db/db mice, 4.8% HbA$_{1c}$ was glycosylated. However, by 12 to 14 weeks of age, this had risen to 7.3% of HbA$_{1c}$ in untreated db/db mice. In contrast, 6.3%, 6% and 5.6% of HbA$_{1c}$ were glycosylated in the blood of age-matched mice following treatment with 2.5 mgkg$^{-1}$ glimepiride, 0.5 mgkg$^{-1}$ and 2.5 mgkg$^{-1}$ cytopiloyne, respectively (FIG. 1E). These data suggest that cytopiloyne (decrease of glycosylated HbA$_{1c}$ by 1.3% and 1.7%) achieved a relatively better glycemic control than glimepiride (decrease of glycosylated HbA$_{1c}$ by 1%) in db/db mice. Diabetic db/db mice usually develop severe atrophy of pancreatic islets. We assessed the protective effect of cytopiloyne on islet destruction in db/db mice aged 8 weeks and 16 weeks, which corresponded to early and chronic stages of diabetes, respectively. There was no significant difference in pancreatic islets of treated and untreated db/db mice at 6 to 8 weeks of age. Twelve- to 14-week-old db/db mice, which had received a long-term treatment with vehicle control and glimepiride, had sporadic islets. In a sharp contrast, the age-matched db/db mice with cytopiloyne treatment showed much greater preservation of islet structure (FIG. 1F, images e, f, g, h and m, n, o, p). We next examined the preventive effect of cytopiloyne on T2D in db/db mice. Cytopiloyne failed to prevent the disease in db/db mice, but it did control blood sugar in these mice much better than the control (Table 1). Collectively speaking, cytopiloyne treatment for diabetes was better than glimepiride in terms of both dosage and therapeutic effect.

Table 1 shows the blood glucose levels following a single oral dose of cytopiloyne in fed db/db mice. Diabetic db/db mice aged 6 to 8 weeks were grouped, fasted for 12 h, allowed free access to food for 2 h, and removed from food. One half hour after food removal was set as time 0. Postprandial blood was collected from the tail vein of the mice, tube-fed with vehicle, glimepiride (GLM) at 2.5 mg/kg/day and cytopiloyne (CP) at 0.1, 0.5 and 2.5 mg/kg/day. Blood samples were collected at the indicated time intervals (0, 1, 2 and 4 h). The blood glucose levels were determined using a glucometer. The number of mice tested (n) is indicated in parentheses in the first column.

TABLE 1

| | Blood glucose level (mg/dl) | | | |
|---|---|---|---|---|
| Treatment | 0 | 1 | 2 | 4 (h) |
| Vehicle (8) | 365 ± 9 | 309 ± 4 | 281 ± 9 | 240 ± 11 |
| GLM (5) | 378 ± 9 | 237 ± 16* | 178 ± 20* | 187 ± 6* |
| CP 0.1 (7) | 373 ± 6 | 267 ± 12 | 204 ± 17* | 158 ± 18* |
| CP 0.5 (7) | 369 ± 27 | 214 ± 15* | 163 ± 8* | 132 ± 11* |
| CP 2.5 (7) | 365 ± 9 | 207 ± 11* | 147 ± 12* | 129 ± 11* |

*P < 0.05 as determined by ANOVA.

Table 2 shows blood insulin levels following a single oral dose of cytopiloyne in fed db/db mice. The same procedure as Table 1 was performed. Blood samples at the indicated time interval (0, 0.5, 1, 2, and 4 h) were collected from the retroorbital vein of those mice and the insulin levels in each blood sample were determined using ELISA kits. The number of mice used (n) is indicated in parentheses in the first column.

TABLE 2

| Treatment | Blood insulin level (μg/l) | | | | |
|---|---|---|---|---|---|
| | 0 | 0.5 | 1 | 2 | 4 (h) |
| Vehicle (8) | 13.8 ± 1.9 | 11.5 ± 1.9 | 10.3 ± 2.4 | 8.3 ± 0.7 | 8.6 ± 1.9 |
| GLM (6) | 13.9 ± 1.2 | 19.3 ± 4.2 | 26.3 ± 3.3* | 15.9 ± 1.7* | 11.8 ± 2.1* |
| CP 0.1 (5) | 17.2 ± 4.7 | 21.0 ± 1.3* | 15.5 ± 0.6* | 14.1 ± 0.5 | 9.7 ± 1.3 |
| CP 0.5 (5) | 15.7 ± 1.9 | 22.6 ± 1.9* | 16.0 ± 2.4* | 12.8 ± 0.7* | 12.2 ± 1.9 |
| CP 2.5 (5) | 12.5 ± 1.2 | 25.5 ± 1.2* | 18.9 ± 3.3* | 17.6 ± 1.7* | 8.9 ± 2.1 |

*$P < 0.05$ as determined by ANOVA.

Tables 3 and 4 show the effects of cytopiloyne on body weight and food intake in db/db mice, respectively. Diabetic db/db mice at 6 to 8 weeks of age were allowed free access to food. These mice were treated with vehicle, glimepiride (GLM, 2.5 mg/kg/day), or cytopiloyne (CP, 0.5 and 2.5 mg/kg/day). Mean body weight and food intake of each group were measured from 0 to 6 weeks post-treatment. The number of mice (n) is indicated in parentheses.

TABLE 3

| Weeks | Mean body weight (g/mouse) | | | | |
|---|---|---|---|---|---|
| | 0 | 1 | 2 | 4 | 6 |
| Vehicle (6) | 27.7 ± 2.9 | 30.9 ± 3.2 | 33.9 ± 3.6 | 33.7 ± 4.1 | 38.6 ± 3.8 |
| GLM (6) | 26.9 ± 1.2 | 30.3 ± 2.7 | 30.7 ± 3.0 | 35.2 ± 1.8 | 36.3 ± 2.1 |
| CP 0.5 (6) | 28.2 ± 3.0 | 29.7 ± 3.1 | 32.3 ± 3.3 | 34.1 ± 2.9 | 34.8 ± 2.8 |
| CP 2.5 (6) | 27.1 ± 2.4 | 30.0 ± 2.5 | 31.7 ± 1.5 | 33.3 ± 4.1 | 36.4 ± 3.7 |

TABLE 4

| Weeks | Mean food intake (g/mouse/day) | | | | |
|---|---|---|---|---|---|
| | 0 | 1 | 2 | 4 | 6 |
| Vehicle 6) | 4.8 | 4.2 | 4.7 | 7.1 | 7.1 |
| GLM (6) | 4.4 | 4.3 | 5.3 | 6.5 | 6.7 |
| CP 0.5 (6) | 4.9 | 5.9 | 6.5 | 6.6 | 7.0 |
| CP 2.5 (6) | 4.7 | 4.7 | 4.7 | 6.0 | 6.1 |

Cytopiloyne Acts as an Insulin Secretagogue Rather than a Sensitizer

Figure 2A:
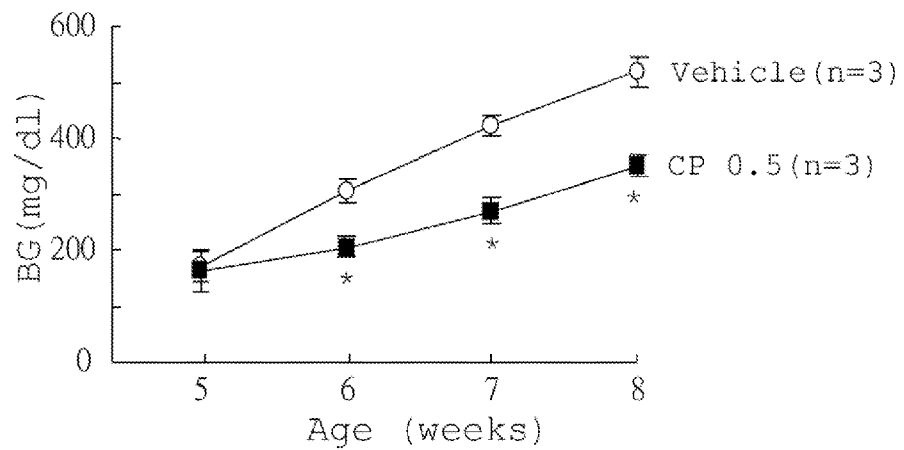
FIGS. 2A-B show the prophylactic effect of cytopiloyne in db/db mice. (A) Two groups of diabetes-free db/db mice aged 4 weeks were daily tube-fed with vehicle (1 µl DMSO per 1 ml of PBS) or cytopiloyne (CP, 0.5 mgkg$^{-1}$) for 4 weeks. Postprandial blood glucose levels in these mice were measured. (B) Blood insulin levels from the mice of FIG. 1A were measured. Results from 3 independent experiments are expressed as mean±SEM, and P<0.05 was considered to be statistically significant (*).
Figure 2B:
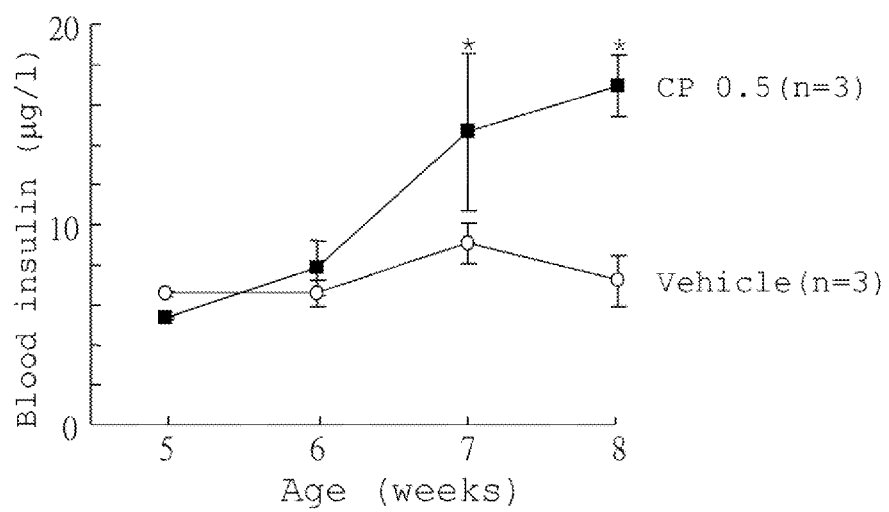

The sugar-reducing and insulin-increasing effects of cytopiloyne raised the possibility that cytopiloyne controlled blood sugar in db/db mice mainly via insulin production from β-cells. Rat primary pancreatic islets are commonly used to test insulin release/synthesis because rats have more abundant pancreatic islets than mice and the islets of both species respond to glucose similarly. To examine the role of cytopiloyne in insulin release, rat islets were treated with cytopiloyne at different concentrations in KRB buffer containing 16.7 mM glucose. It was found that cytopiloyne enhanced insulin secretion in high glucose medium (FIG. 2A) as well as in glucose-free and low glucose media. Cytopiloyne increased insulin release (FIG. 2B).

Figure 3B:
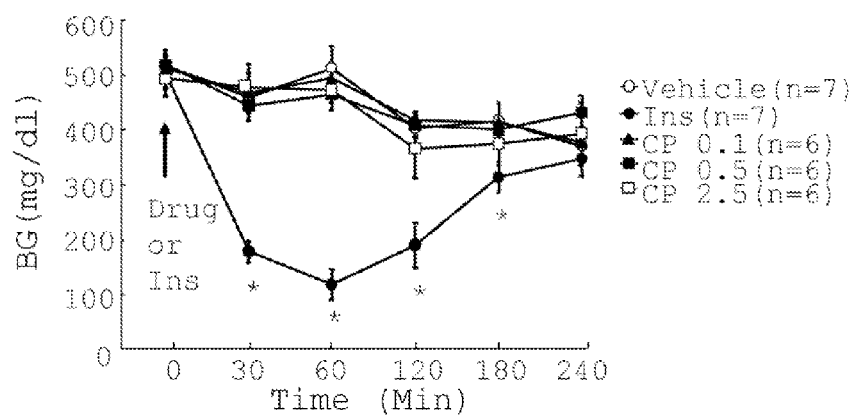

To further examine the in vive response where cytopiloyne reduced hyperglycemia via insulin production from pancreatic β-cells, we tested its ability to reduce hyperglycemia and to augment insulin levels in STZ-treated C57BL mice whose β-cells were depleted. As expected, cytopiloyne lost its ability in regulating both responses in the above mice (FIG. 3B). In contrast, insulin treatment still diminished blood glucose levels in the β-cell-depleted mice (FIG. 3B).

Figure 3C:
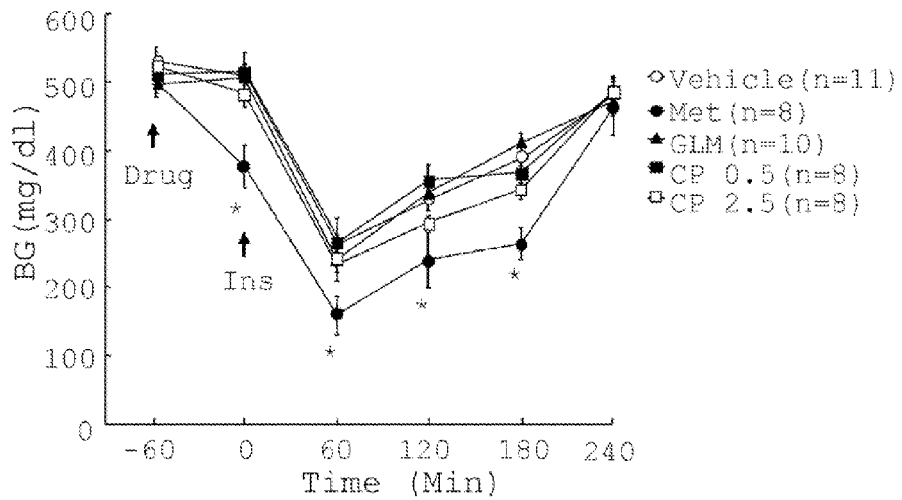

To further test the possibility that cytopiloyne is an insulin sensitizer, we administrated STZ-treated C57BL mice with an oral dose of vehicle, glimepiride, metformin or cytopiloyne 60 min before an insulin injection. Both cytopiloyne and glimepiride had little, if any, lowering effect on blood sugar in these mice. However, metformin, an insulin sensitizer, significantly reduced blood glucose levels compared to vehicle alone in these mice (FIG. 3C). Overall, our results support an insulin-releasing role of cytopiloyne in β-cells.

Cytopiloyne Elevates the Level of Insulin mRNA and Protein in Pancreatic Islets

Figure 4A:
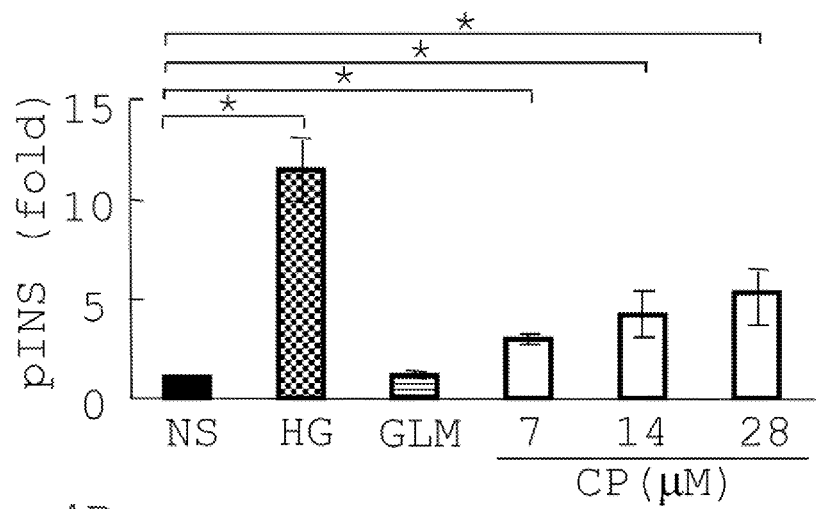
FIGS. 4A-C show an increase in insulin mRNA and protein content by cytopiloyne in pancreatic islet cells. (A) HIT-T15 β-cells transfected with phINS-Luc and pRL-TK plasmids were incubated with vehicle (NS), glimepiride (GLM, 10 µM), high glucose (HG, 16.7 mM) or cytopiloyne at 7, 14 or 28 µM. Ten µg of cell lysates from these cells underwent to dual luciferase assays. (B) The relative expression level (R.E.L.) of insulin relative to L13 in rat primary pancreatic islet cells, which were already treated with vehicle (NS), high glucose (HG, 16.7 mM), glimepiride (GLM, 10 µM) or cytopiloyne (CP, 7, 14 or 28 µM) for 24 h, were determined by real-time RT-PCR. (C) Rat pancreatic islet cells were treated with vehicle, glucose (3.3 mM (LG) or 16.7 mM (HG)) or cytopiloyne (CP, 7, 14 and 28 µM) in the presence of brefeldin A for 24 h. After anti-insulin antibody staining, these cells underwent FACS analysis. The percentage of insulin-positive β-cells is shown. All the results from 3 independent experiments are expressed as mean±SEM, and P<0.05 was considered to be statistically significant (*).
Figure 4B:
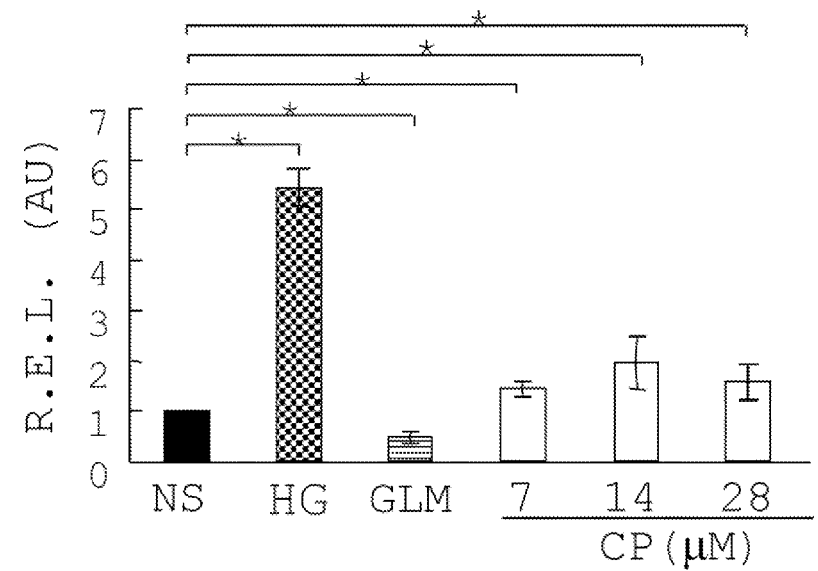
Figure 4C:
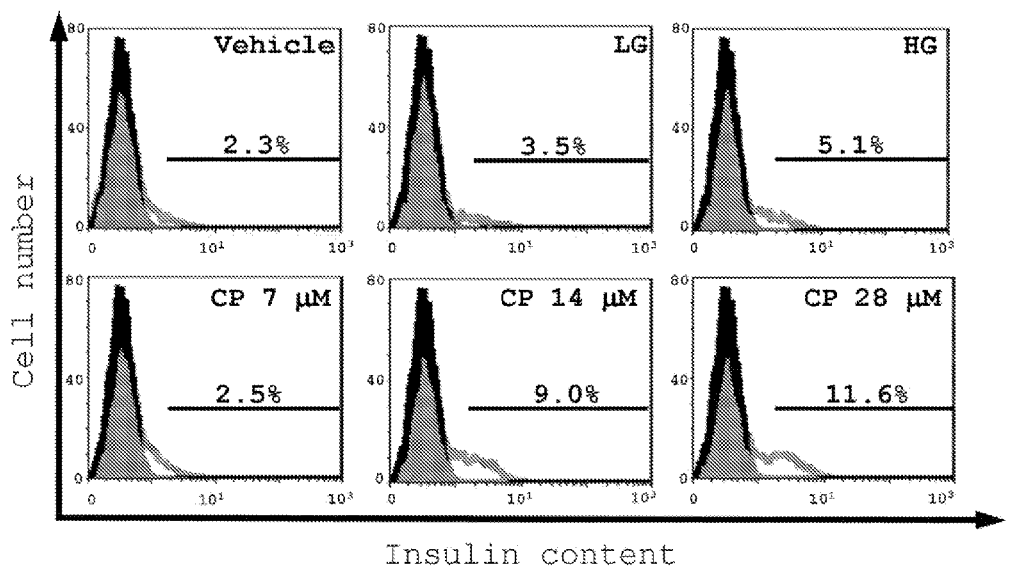

Glucose has been known to modulate transcription, translation and secretion of insulin in pancreatic β-cells. However, current secretagogues always increase insulin secretion but not synthesis. It has been shown that cytopiloyne increases insulin release from rat islets (FIG. 2A). To evaluate the effect of cytopiloyne on insulin expression, an insulin promoter-driven reporter construct was used to test cytopiloyne's effect on insulin transcription. Glimepiride had no significant effect on insulin transcription in HIT-T15 β-cells compared to the control. In contrast, 16.7 mM glucose up-regulated insulin transcription 11 times, and 28 μM cytopiloyne augmented insulin transcription by 5 times, and this increase was dose-dependent (FIG. 4A). Next, the expression levels of insulin mRNA relative to those of L13 mRNA, a house-keeping control, were examined in rat islet cells pre-treated with vehicle control, 16.7 mM glucose, 10 μM glimepiride or cytopiloyne at 7, 14 and 28 μM for 24 h. Glimepiride could not elevate but slightly decreased insulin transcription. In contrast, 16.7 mM glucose up-regulated insulin transcription to 5 times, and 28 μM cytopiloyne augmented insulin transcription to around 2 times (FIG. 4B). In addition, the effect of cytopiloyne on insulin content inside pancreatic islet cells were examined. Glucose (16.7 mM) treatment increased the intracellular insulin levels in these cells to 220% of vehicle treatment (FIG. 4C). Consistent with cytopiloyne's effect on insulin transcription, 28 μM cytopiloyne increased the intracellular insulin levels fivefold compared to the vehicle treatment in these cells, and this effect on insulin content was dose-dependent (FIG. 4C). The data suggest that cytopiloyne stimulates insulin expression in pancreatic β-cells.

Figure 5A:
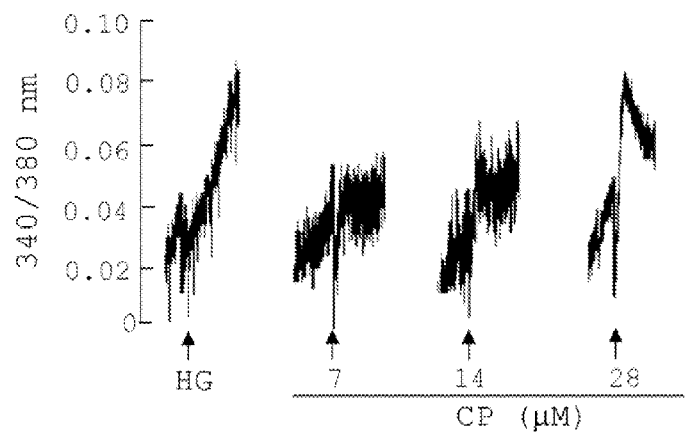
FIGS. 5A-D show the effects of cytopiloyne on calcium mobilization, DAG generation and PKCα activation. (A) After Fura 2-AM loading, RIN-m5F cells were stimulated with 16.7 mM glucose (HG) and cytopiloyne at 7, 14 and 28 µM. Level of intracellular calcium, as shown by the 340/380 nm ratio, was detected using a fluorescence spectrophotometer. (B) RIN-m5F cells were pulsed with $^3$H-myristic acid (5 Ciml$^{-1}$) for 16 hours. After washing, the cells were stimulated with glucose, cytopiloyne, PMA and glimepiride. Total lipids were separated on a silica thin layer plate. DAG and cholesterol were visualized with iodine vapor and identified by their standards. (C) RIN-m5F cells were incubated with vehicle (Mock), cytopiloyne (CP, 3, 7 and 14 µM), PMA (1 µM) and 16.7 mM (HG). Membrane or cytosolic proteins were subjected to Western blot with anti-PKCα and anti-Actin antibodies. (D) RIN-m5F cells were incubated with vehicle (Mock), cytopiloyne (CP 7 µM) and PMA (1 µM). After lysis, total lystaes were subjected to Western blot with anti-PKCα, anti-phospho-PKCα and anti-Actin antibodies.
Figure 5B:
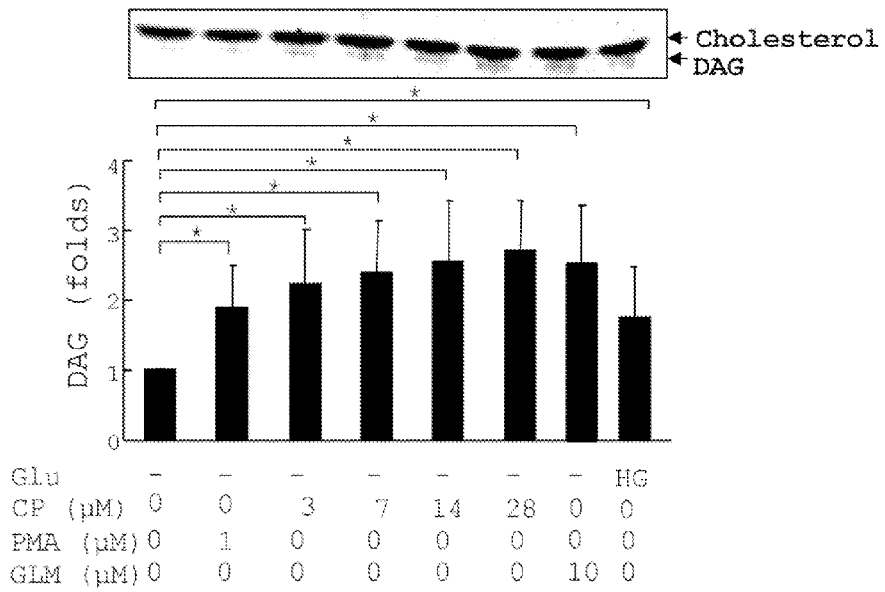
Figure 5C:
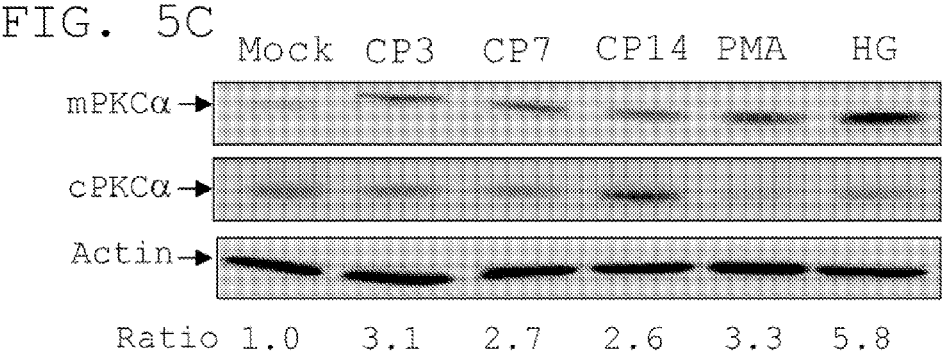
Figure 5D:
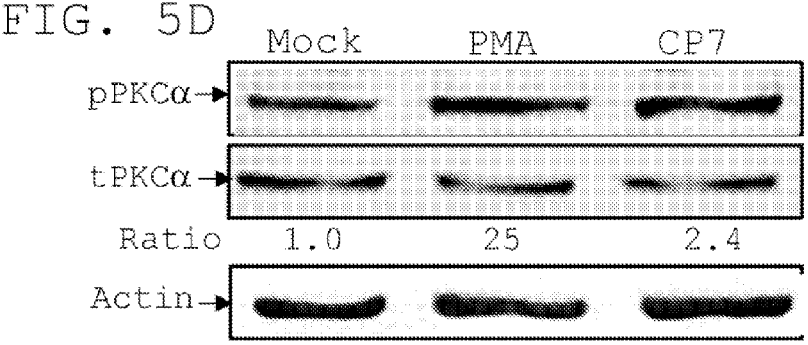

Cytopiloyne Increases Calcium Influx, Diacyl Glycerol (DAG) Generation and Protein Kinase C Alpha (PKCα) Activation Secondary messengers such as calcium and DAG are involved in a variety of signaling pathways in β-cells. To further understand the mechanism by which cytopiloyne increased the gene expression and release of insulin in β-cells, we first examined its effect on calcium mobilization in RIN-m5F cells, a rat β-cell line. It was found that 16.7 mM glucose significantly increased intracellular calcium in β-cells (FIG. 5A). Similarly, cytopiloyne increased intracellular calcium in a dose-dependent manner (FIG. 5A). Next, the effect of cytopiloyne on the production of lipids, DAG and cholesterol, in RIN-m5F cells were examined. PMA, glimepiride and 16.7 mM glucose significantly increased the level of DAG in comparison with the vehicle control (FIG. 5B). It is noteworthy that cytopiloyne dose-dependently increased the level of DAG but not cholesterol (FIG. 5B). PKCα was reported to be implicated in insulin secretion of β-cells. We investigated the effect of cytopiloyne on PKCα activation, as evidenced by its translocation and phosphorylation. As expected, PMA and 16.7 mM glucose increased the translocation of PKCα from cytoplasm to membrane (FIG. 5C). It was the case for cytopiloyne (FIG. 5C). Besides, PMA, 16.7 mM glucose and cytopiloyne increased phosphorylation of PKCα. The data indicated that cytopiloyen activate PKCα through an increase of its activators, calcium and DAG.

Cytopiloyne Increases Insulin Secretion and Transcription Via PKCα

Next, we tested whether PKCα regulates cytopiloyne-mediated insulin secretion. It was found that like positive controls, 16.7 mM glucose and phorbol 12-myristate 13-acetate (PMA), cytopiloyne stimulated insulin secretion in HIT-T15 cells (FIG. 6A). In contrast, GF109203X, a PKC inhibitor, inhibited cytopiloyne- and PMA-induced insulin secretion (FIG. 6A). It was also found that overexpression of dominant-negative mutant of PKCα decreased cytopiloyne- and PMA-mediated insulin secretion to a greater extent than high glucose-mediated insulin secretion (FIG. 6B). In addition, we also tested the involvement of PKCα in insulin transcription in HIT-T15. It was found that like 16.7 mM glucose and PMA, cytopiloyne stimulated insulin transcription in HIT-T15 cells (FIG. 6C). GF109203X, a PKC inhibitor, completely abolished cytopiloyne-, glucose- and PMA-mediated insulin transcription (FIG. 6C). Similarly, overexpression of dominant-negative PKCα significantly inhibited the transcription (FIG. 6D). The data suggest that PKCα participate cytopiloyne-mediated insulin secretion and expression in β-cells.

Cytopiloyne does not Cause Adipogenesis in 3T3-L1 Cells

Figure 8:
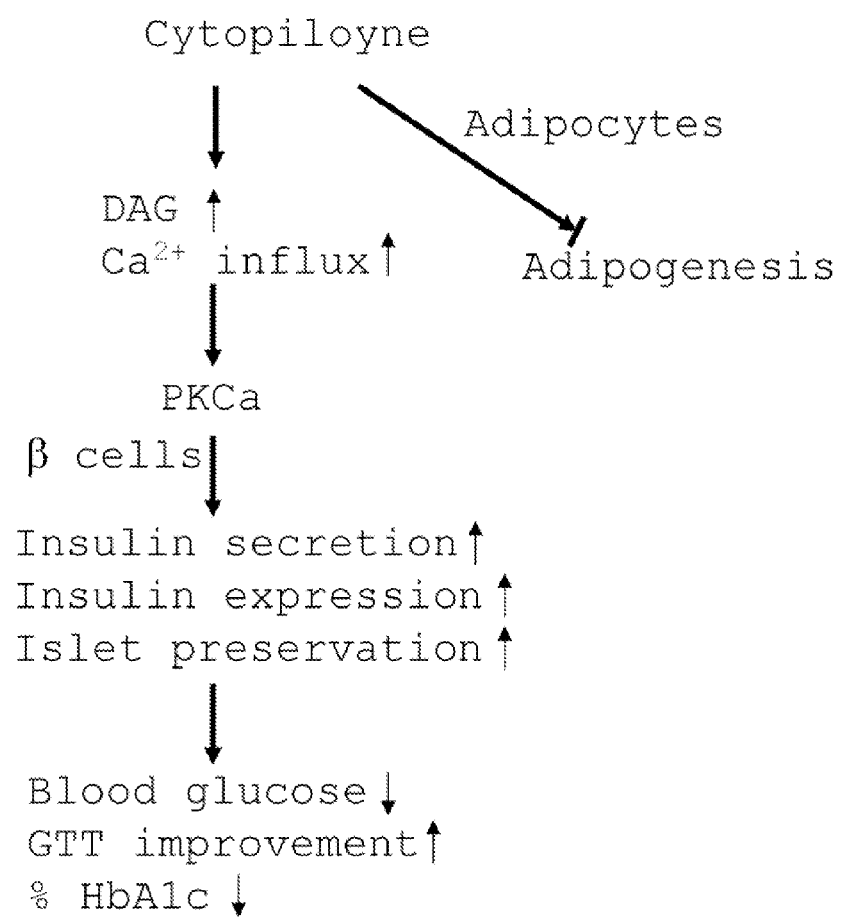
FIG. 8 is a model to illustrate the pharmacological actions of cytopiloyne in T2D. Cytopiloyne possesses in vivo antidiabetic effects, as evidenced by reduction of blood sugar and glycosylated $HbA_{1c}$, and improvement of GTT, and its regulation of β-cell functions, as evidenced by insulin secretion, insulin expression and pancreatic islet protection. As well, cytopiloyne has a neutral effect on adipogenesis in 3T3-L1 adipocytes.

Anti-diabetic agents such as glimepiride, meglitinides and rosiglitazone usually induce accumulation of lipid droplets in adipose tissues, leading to undesirable weight gain and an elevation of insulin resistance in the body. To test whether cytopiloyne has this side effect, the potential to induce adipogenesis was examined in differentiating 3T3-L1 cells. The lipid droplets from adipocytes were visualized with Oil red O and examined by light microscopy. It was found that both glimepiride (10 μM) and rosiglitazone (1 μM) induced significant lipid accumulation in these cells (FIG. 7A-i, top panel, and FIG. 7A-ii). In contrast, cytopiloyne at a high dose (50 μM) only showed the same basal level of lipid droplets as the control (FIG. 7A-i, bottom panel, and FIG. 7A-ii). The lipid contents of these cells, counted as amount of Oil red O, were quantified using a spectrophotometer (bottom panel, FIG. 7A-ii). To confirm the effect of cytopiloyne on adipogenesis, the expression levels of adipocyte protein 2 (aP2) and adiponectin genes, two adipose cell differentiation markers, were examined in 3T3-L1 cells. It has been reported that glimepiride and rosiglitazone increased aP2 expression to 31 and 11 times of the control, respectively. In contrast, cytopiloyne had little effect on aP2 expression (FIG. 7B-i). Similarly, glimepiride and rosiglitazone elevated adiponectin expression level to 9 and 21 times control levels. Again, cytopiloyne had a slight reduction in adiponectin expression (FIG. 7B-ii). Overall, the results suggest that cytopiloyne had little effect on adipogenesis. FIG. 8 describes a plausible scheme by which cytopiloyne treats type 2 diabetes (T2D).

Discussion

The above data have not only demonstrated the anti-diabetic efficacy of cytopiloyne but also uncovered the biological mechanism of the anti-diabetic actions of cytopiloyne in cell and mouse models. Compared with sulfonylureas, cytopiloyne is a relatively potent anti-diabetic compound, as evidenced by glycemic regulation, glucose tolerance test and glycosylation of $HbA_{1c}$ in the db/db mouse model. Its anti-diabetic mechanism may be attributed to insulin augmentation and islet protection.

Cytopiloyne has several unique benefits over current secretagogues in the market, including enhancement of insulin expression, maintenance of islet architecture, and neutral effect on adipogenesis. Firstly, nutrients such as glucose can stimulate insulin biosynthesis at transcriptional and translational levels and secretion of insulin in β-cells. However, current secretagogues for diabetes can stimulate insulin secretion but cannot stimulate insulin biosynthesis. Unexpectedly, cytopiloyne could increase the level of insulin mRNA and protein, which may be functionally superior to sulfonylureas (FIG. 4A-B). Secondly, cytopiloyne protected islet structure in db/db mice with chronic diabetes (FIG. 1F). Whether or not cytopiloyne employs the same mechanism in prevention of β-cell death in both types of diabetes needs to be further ascertained. Thirdly, insulin secretagogues (e.g., glimepiride, glibenclamide and meglitinide) and the sensitizer, thiazolidinedione, are known to cause adipogenesis and weight gain in diabetic mouse models and in patients. Such an increase in body weight worsens insulin resistance in animals and humans. Cytopiloyne did not have this side effect in 3T3-L1 adipocytes, as shown by accumulation of oil droplets and adipocyte differentiation markers. (FIGS. 7A-B), which was consistent with the observation that 6-week-treatment with cytopiloyne did not significantly increase body weight in db/db mice compared to control mice (Tables 3-4).

Cytopiloyne has other advantages over glimepiride. Cytopiloyne has similar anti-diabetic effects as glimepiride at one fifth of the dose, and modestly better anti-diabetic effects at the same dose (Table 1 and FIG. 1B). In comparison with the low potency insulin secretagogues, cytopiloyne may have other benefits such as increased efficacy or decreased toxicity. Cytopiloyne may have a different mechanism of action from glimepiride, based on the huge difference in their chemical structures. Cytopiloyne (FIG. 1A) is structurally distinguishable from currently known secretagogues, which may represent a new category of anti-diabetic agents. Thus, identification of the receptor(s) for cytopiloyne is necessary to understand both its anti-diabetic mechanism and to discover new pathways in insulin synthesis/secretion and islet preservation.

Cytopiloyne protected against islet atrophy in db/db mice even at the low dose 0.5 mgkg$^{-1}$ day$^{-1}$ (FIG. 1F, images e, f, m, n). Glimepiride failed to provide such a protection (FIG. 1F, images c, d and k, l). The db/db mouse has an inherited predisposition to sever obesity-associated metabolic syndrome caused by a mutation in the leptin receptor-b. It has been reported that the level of adipogenesis is a key determinant of both age of onset and severity of the metabolic syndrome in both normal mice and in db/db mice (Wang et al., 2008). In both rodent and humans, lipids have been shown to accumulate in the organs that are most affected in metabolic syndrome. In addition, ectopic lipids overload has been demonstrated to disable and destroy normal cardiomyocytes and pancreatic β-cells through the process of lipoapoptosis (Wang et al., 2008). Therefore, cytopiloyne may protect pancreatic β-cells from destruction caused by lipoapotosis in patients having metabolic syndrome.

Current secretagogues occasionally reduce blood sugar to a detrimental degree, a situation known as hypoglycemia. Therefore, the development of blood glucose-dependent secretagogues would prevent this significant adverse effect. At a low dose (e.g., 3 μM), cytopiloyne simulates insulin release in pancreatic islets in a glucose-dependent manner (FIG. 3A-i, ii and iii). However, a high dose of cytopiloyne can still stimulate insulin secretion to some extent even in the absence of glucose (FIG. 3A-i). The data show that cytopiloyne-mediated insulin release is partially glucose-dependent. Thus, cytopiloyne at a high dose may have a similar potential risk for hypoglycemia as sulfonylureas, particularly in patients with low blood glucose levels. However, this problem can be alleviated by decreased dosage or the combined use of a sensitizer such as metformin, which has no hypoglycemic effect. Although cytopiloyne has this imperfection, it is still a potential lead compound for diabetes based on the aforementioned beneficial effects. It should also be noted that insulin secretagogues are clinically in broad use without dramatic incidence of hypoglycemia because the patients with T2D usually have higher insulin resistance than normal subjects.

Figure 1B:
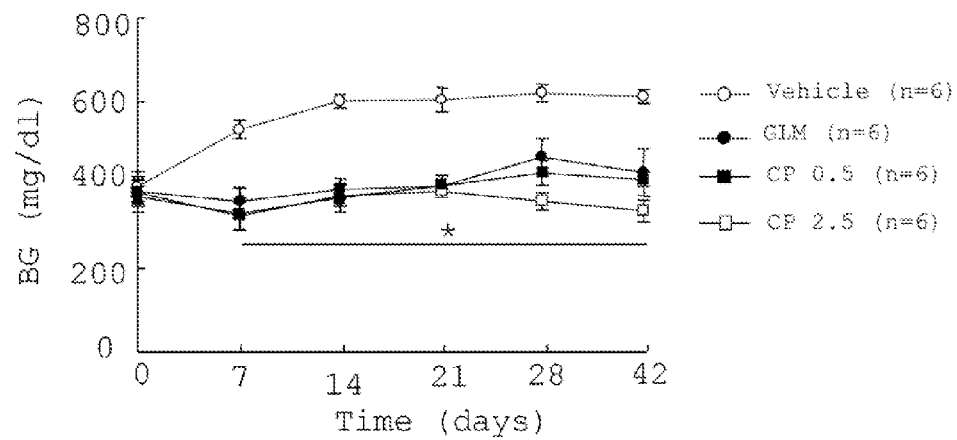
Figure 1C:
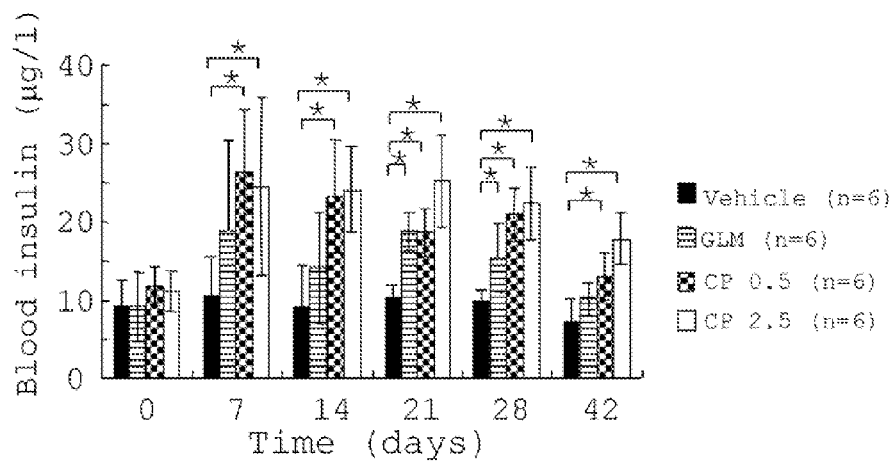
Figure 1E:
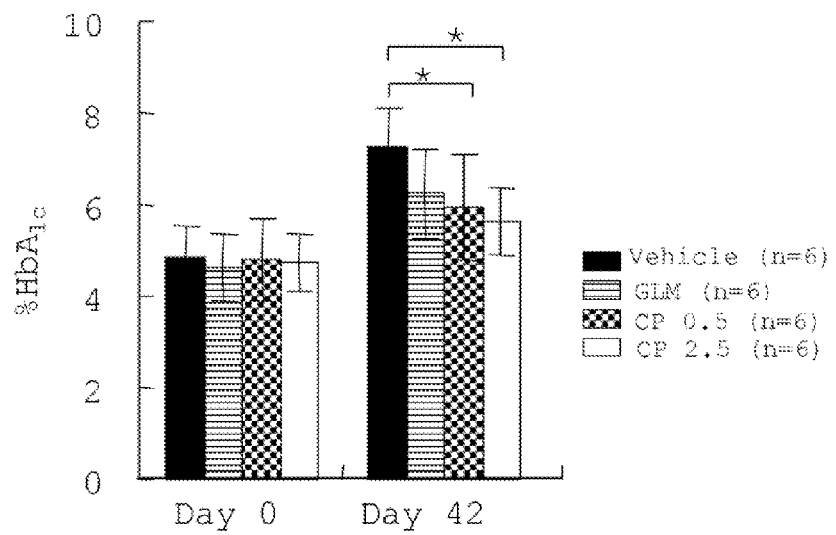
Figure 1F:
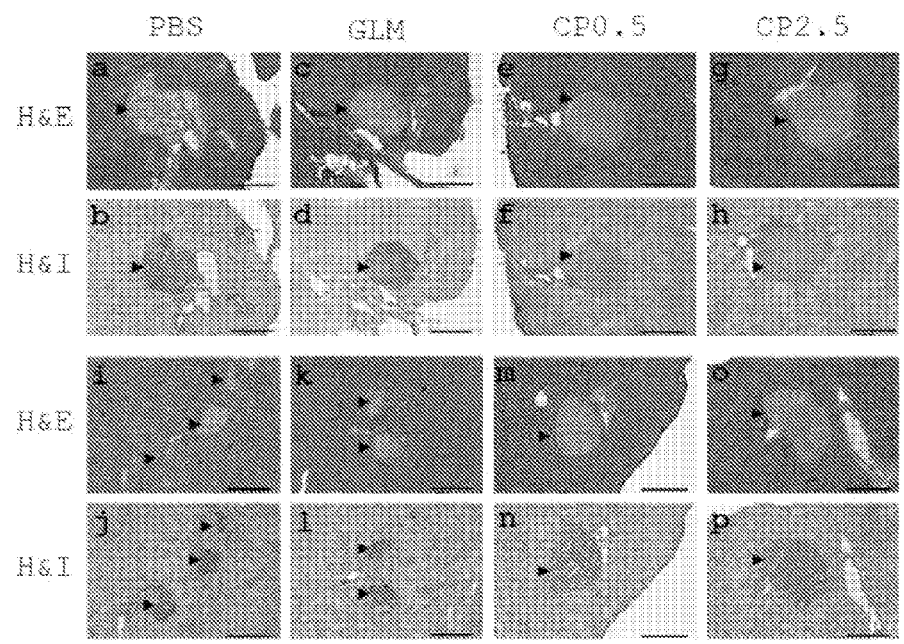

Cytopiloyne has a glucose moiety (FIG. 1A). It is possible that its glucose residue may act on the glucose receptors to mediate insulin expression and secretion. However, our data argue against this possibility. The ratio of glucose in 28 μM cytopiloyne (containing 28 μM glucose) to 16.7 mM glucose is 1 to 594. In contrast, Up-regulation of insulin transcription by 28 μM cytopiloyne is 40% (not 0.17%) the up-regulation of insulin transcription by 16.7 mM glucose (FIGS. 4A-B). Besides, the glucose residue in cytopiloyne did not appear to be important for the function of cytopiloyne. Although cytopiloyne aglycone was less effective than cytopiloyne in inducing insulin secretion, the aglycone did stimulate insulin secretion in β-cell line to some extent (unpublished data). Note-worthily, 28 μM cytopiloyne was less effective on insulin mRNA production but more effective on increase in insulin content than 16.7 mM glucose in islets (FIGS. 4A-B). This discrepancy may be due to a differential potency in regulation of mRNA and protein of insulin by cytopiloyne. It has been reported that glucose and GLP-1 strongly stimulate insulin translation while only modestly stimulate insulin transcription in β-cells.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

Chang, C L, Chang, S L, Lee, Y M, Chiang, Y M, Chuang, D Y, Kuo, H K, Yang, W C (2007) "Cytopiloyne, a polyacetylenic glucoside, prevents type 1 diabetes in nonobese diabetic mice" *J Immunol* 178(11): 6984-6993.

Chang, S L, Chang, C L, Chiang, Y M, Hsieh, R H, Tzeng, C R, Wu, T K, Sytwu, H K, Shyur, L F, Yang, W C (2004) "Polyacetylenic compounds and butanol fraction from *Bidens pilosa* can modulate the differentiation of helper T cells and prevent autoimmune diabetes in non-obese diabetic mice" *Planta Med* 70(11): 1045-1051.

Chien, S C, Young, P H, Hsu, Y J, Chen, C H, Tien, Y J, Shiu, S Y, Li, T H, Yang, C W, Marimuthu, P, Tsai, L F, Yang, W C (2009) "Anti-diabetic properties of three common *Bidens pilosa* variants in Taiwan" *Phytochemistry* 70(10): 1246-1254.

Egan, J M, Bulotta, A, Hui, H, Perfetti, R (2003) "GLP-1 receptor agonists are growth and differentiation factors for pancreatic islet beta cells" *Diabetes Metab Res Rev* 19(2): 115-123.

Hsu, Y J, Lee, T H, Chang, C L, Huang, Y T, Yang, W C (2009) "Anti-hyperglycemic effects and mechanism of *Bidens pilosa* water extract" *J Ethnopharmacol* 122(2): 379-383.

Krentz, A J, Bailey, C J (2005) "Oral antidiabetic agents: current role in type 2 diabetes mellitus" *Drugs* 65(3): 385-411.

Purnell, J Q, Weyer, C (2003) "Weight effect of current and experimental drugs for diabetes mellitus: from promotion to alleviation of obesity" *Treat Endocrinol* 2(1): 33-47.

Ubillas, R P, Mendez, C D, Jolad, S D, Luo, J, King, S R, Carlson, T J, Fort, D M (2000) "Antihyperglycemic acetylenic glucosides from *Bidens pilosa*" *Planta Med* 66(1): 82-83.

Wang, May-Yun, Grayburn, Paul, Chen, Shuyuan, Ravazzola, Mariella, Orci, Lelio, and Unger, Roger H. (2008) "Adipogenic capacity and the susceptibility to type 2 diabetes and metabolic syndrome" *PNAS* 105(16): 6139-6144.

What is claimed is:

1. A method of protecting against atrophy of pancreatic islets, comprising:
administering a pharmaceutical composition comprising:
(a) an effective amount of a compound of formula (I)

$$H_3C\text{--}(C{\equiv}C)_m\text{--}(\underset{H}{C}{=}\underset{H}{C})_n\text{--}(\ )_o\text{--}\overset{OGlu}{\underset{}{C}}\text{--}(\ )_p\text{--}OR,\qquad (I)$$

wherein
R is H or COCH2COOH;
m=3 or 4;
n=0 or 1;
o=2; and
p=1 or 2, and
(b) a pharmaceutically acceptable carrier;
to a human who has any three of the following conditions:
i) waist measurement of 40 inches or more for men and 35 inches or more for women;
ii) triglyceride levels of 150 milligrams per deciliter (mg/dL) or above, or taking medication for elevated triglyceride levels;
iii) HDL cholesterol level below 40 mg/dL for men and below 50 mg/dL for women, or taking medication for low HDL levels; and
iv) blood pressure levels of 130/85 or above, or taking medication for elevated blood pressure levels.

2. The method of claim 1, wherein the effective amount of the compound for protection against atrophy of pancreatic islets is a human equivalent dose of about 2.5 mg/Kg×(0.020 Kg/weight of the human in Kg)$^{0.33}$ and the administering step is performed per day for 2 or more weeks.

3. The method of claim 1, wherein the composition comprises cytopiloyne having a chemical structure of formula (II):

$$\text{(II)}\quad\text{---}{\equiv}\text{---}{\equiv}\text{---}{\equiv}\text{---}{\equiv}\text{---}\overset{OGlc}{\underset{OH.}{\diagdown}}$$

4. The method of claim 1, wherein the composition comprises a *Bidens pilosa* extract comprising cytopiloyne.

5. The method of claim 1, in which the method is without causing an increase in body weight and/or without causing accumulation of lipid contents in the adipose tissues of the human.

6. The method of claim 1, in which the method is without causing development of insulin resistance in the human.

7. The method of claim 1, wherein the administering step is performed daily for no less than 10 weeks.

8. The method of claim 1, wherein the administering step is performed daily for 4 weeks or more.

9. The method of claim 1, wherein the compound is at least one selected from the group consisting of $$\text{(II)}\quad\text{---}{\equiv}\text{---}{\equiv}\text{---}{\equiv}\text{---}{\equiv}\text{---}\overset{OGlc}{\underset{OH,}{\diagdown}}$$

$$\text{(III)}\quad\text{---}{\equiv}\text{---}{\equiv}\text{---}{\equiv}\text{---}{\equiv}\text{---}\overset{OGlc}{\underset{OR,}{\diagdown}}$$

R = COCH2COOH

-continued
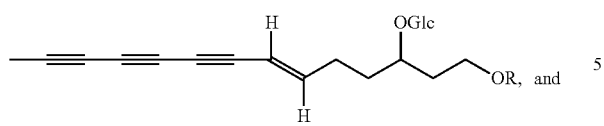
(IV)
R= COCH2COOH
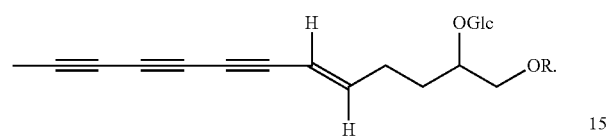
(V)
R = COCH2COOH
10. The method of claim 1, wherein the composition comprises cytopiloyne purified from a *Bidens pilosa* extract.
11. The method of claim 1, wherein the administering step is performed daily at a human equivalent dose of about 0.5 mg/Kg×(0.020 Kg/weight of the human in Kg)$^{0.33}$ or more for a first treatment course of 6 weeks.
* * * * *